US011583451B2

(12) United States Patent
Jacobs et al.

(10) Patent No.: US 11,583,451 B2
(45) Date of Patent: Feb. 21, 2023

(54) UNIT FOR HEMOSTASIS AND ARRANGEMENT CONTAINING THE SAME

(71) Applicant: BIOCER ENTWICKLUNGS-GMBH, Bayreuth (DE)

(72) Inventors: Alexander Jacobs, Villingen-Schwenningen (DE); Frank Heidenau, Pegnitz (DE)

(73) Assignee: BIOCER ENTWICKLUNGS-GMBH, Bayreuth (DE)

(*) Notice: Subject to any disclaimer, the term of this patent is extended or adjusted under 35 U.S.C. 154(b) by 1118 days.

(21) Appl. No.: 16/303,315

(22) PCT Filed: May 24, 2017

(86) PCT No.: PCT/EP2017/062641
§ 371 (c)(1),
(2) Date: Nov. 20, 2018

(87) PCT Pub. No.: WO2017/202974
PCT Pub. Date: Nov. 30, 2017

(65) Prior Publication Data
US 2019/0209389 A1    Jul. 11, 2019

(30) Foreign Application Priority Data
May 24, 2016    (EP) .................................... 16171003

(51) Int. Cl.
*A61F 13/36* (2006.01)
*A61F 13/00* (2006.01)
*A61F 15/00* (2006.01)

(52) U.S. Cl.
CPC ........ *A61F 13/36* (2013.01); *A61F 13/00021* (2013.01); *A61F 13/00034* (2013.01);
(Continued)

(58) Field of Classification Search
CPC .......... A61F 13/36; A61F 13/00; A61F 15/00; A61F 13/00021; A61F 13/00034;
(Continued)

(56) References Cited

U.S. PATENT DOCUMENTS

| 8,828,050 B2 | 9/2014 | Gregory |
| 9,381,270 B2 | 7/2016 | Makower et al. |

(Continued)

FOREIGN PATENT DOCUMENTS

| RU | 2505320 C2 | 1/2014 |
| WO | 10129587 A1 | 11/2010 |
| WO | 2010129587 A1 | 11/2010 |

OTHER PUBLICATIONS

Office Action in corresponding EP application 17724594.1 dated Sep. 23, 2020 (pp. 1-2).
(Continued)

*Primary Examiner* — Tatyana Zalukaeva
*Assistant Examiner* — Ilya Y Treyger
(74) *Attorney, Agent, or Firm* — Millen, White, Zelano & Branigan, PC; Ryan Pool; William F. Nixon

(57) ABSTRACT

The invention relates to a unit for hemostasis. The unit is configured to be directly applied to a bleeding wound and comprises an envelope enclosing an inner space as well as an effective amount of a hemostatic material disposed within the inner space. Furthermore, the invention relates to an arrangement of two or more such units for hemostasis, the units being coupled to each other. Moreover, the invention relates to a method for producing an arrangement of units for hemostasis. In accordance with the method, an effective amount of a hemostatic material is disposed within an interior region of a starting material, and neck regions are formed on both sides of the charge so as to form an envelope enclosing the charge.

23 Claims, 10 Drawing Sheets

(52) U.S. Cl.
CPC .. *A61F 13/00063* (2013.01); *A61F 13/00072* (2013.01); *A61F 15/002* (2013.01); *A61F 2013/00093* (2013.01); *A61F 2013/00463* (2013.01)

(58) Field of Classification Search
CPC .......... A61F 13/00063; A61F 13/00072; A61F 15/002; A61F 2013/00093; A61F 2013/00463
See application file for complete search history.

(56) References Cited

U.S. PATENT DOCUMENTS

| 9,656,050 | B2 | 5/2017 | Gregory |
| 2007/0021703 | A1 | 1/2007 | McCarthy |
| 2008/0071207 | A1 | 3/2008 | de Luis et al. |
| 2008/0139988 | A1 | 6/2008 | Dayan et al. |
| 2009/0062233 | A1 | 3/2009 | Ji et al. |
| 2011/0077682 | A1 | 3/2011 | Gregory |
| 2012/0095419 | A1 | 4/2012 | Riesinger |
| 2014/0142523 | A1 | 5/2014 | Steinbaugh et al. |
| 2015/0057696 | A1 | 2/2015 | Gregory |
| 2017/0259049 | A1 | 9/2017 | Gregory |

OTHER PUBLICATIONS

Office Action in corresponding Chinese Patent Application No. 2017800323461 dated Sep. 8, 2020 (pp. 1-1) and English language translation thereof (pp. 1-2).
International Search Report for PCT/EP2017/062641 dated Jul. 11, 2017.
Yun, Yeon-Hum et al., "Biodegradability of Chemically Modified Starch (RS4)/PVA Blend Films: Part 2" J. Polym. Environ., 2008, vol. 16, pp. 12-18.
Office Action in corresponding RU application No. 2018141258/14 dated Aug. 16, 2021 (pp. 1-5).
Office Action in corresponding Chinese Patent Application No. 2017800323461 dated Jun. 15, 2021 (pp. 1-5) and English language translation thereof (pp. 1-5).
Office Action (pp. 1-6) and Search report in corresponding RU application 2018141258/14(068727) dated Jun. 23, 2020 (pp. 1-2).
Office Action in corresponding CA Application No. 3,023,424 dated Oct. 18, 2022 (pp. 1-4).

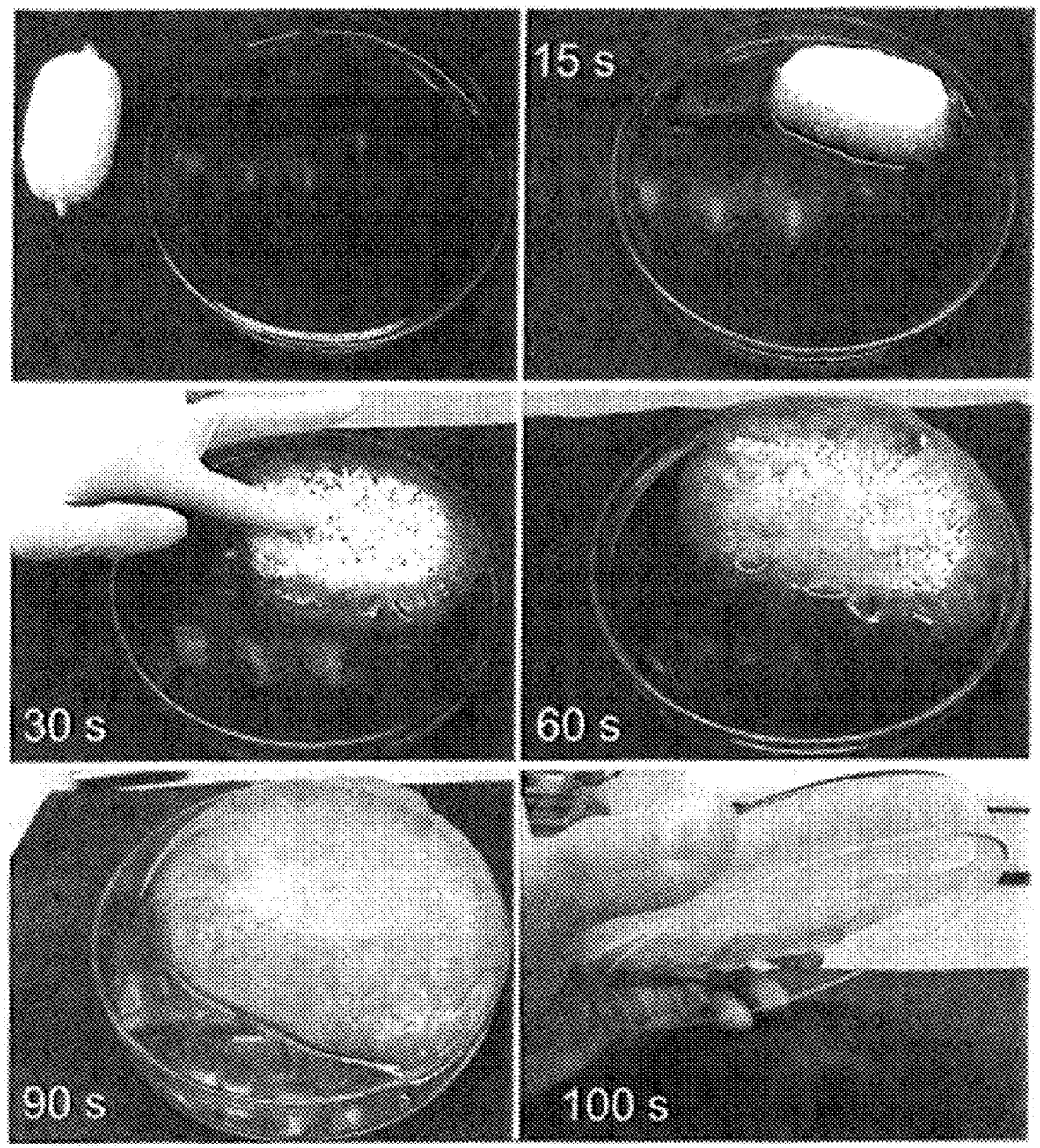
Fig. 13 A-F

UNIT FOR HEMOSTASIS AND ARRANGEMENT CONTAINING THE SAME

The present invention is directed to a unit for hemostasis and an arrangement of two or more units for hemostasis. The present invention is further directed to a method for producing such an arrangement of units for hemostasis.

BACKGROUND OF THE INVENTION

To date, the application of continuous pressure with gauze bandage remains the preferred primary intervention technique used to block blood flow, especially that from severely bleeding wounds.

It is widely accepted that severe bleeding is the leading cause of death from wounds on the battlefield, accounting for approximately 50 percent of such deaths. It is estimated that one-third of these cases could be prevented with improved hemostatic methods and devices. Such enhanced hemorrhage control would also prove most useful in the civilian population where hemorrhage is the second leading cause of death following trauma.

In attempts to provide products which facilitate the stemming of blood flow from a wound, improved hemostatic products have been developed. Those hemostatic agents are typically presented in the form of solid powders or granules, or as liquids. For example, HaemoCer™ PLUS powder marketed by the applicant incorporates a sophisticated, plant-based polymer that creates ultra-hydrophilic, biocompatible particles. Upon contact with blood, HaemoCer™ PLUS enhances the natural clotting cascade by rapidly dehydrating the blood and accelerating the concentration of platelets, red blood cells and coagulation proteins at the bleeding site. HaemoCer™ PLUS also on blood interaction rapidly produces a gelled matrix that adheres to and forms a mechanical barrier with the bleeding tissue.

All of these forms, being flowable, provide for good contact with the irregular surfaces which are typical of wounds so that good hemostasis can be achieved. However, the flowable nature of particulate of hemostatic agents also renders them relatively difficult to handle in use. It can be a problem to retain the flowable hemostatic agent at the wound site where the stemming of blood flow is required.

Medical units and devices for hemostasis are already known and available on the market. For example, there are products available under the tradename Celox® Rapid Gauze, used to reduce blood loss in the treatment of severe injuries. The Celox® gauze contains blood clotting agents made with chitosan, a natural polysaccharide. Chitosan is bio-degradable and will be converted into materials normally present in the body. However, this process can take several months. The Celox® gauze has a sheet-like form and is directly applied to the wound such as is the case with regular gauze pads.

Further products are available on the market under the tradename QuikClot® such as the QuikClot® Trauma Pad, the Z-Fold hemostatic dressing or the QuikClot® Roll. The like, these products are designed to stop bleeding soon after their application to an open wound and, basically, show a two-dimensional structure as it is the case for conventional bandaging materials. QuikClot® comprises a zeolite compound which absorbs water from the blood flowing from a wound such that the clotting factors present in the blood become concentrated. The zeolite compound is not bioresorbable and thus has to be removed from the wound in a subsequent step.

EP 2 752 204 A1 relates to a hemostatic material comprising a carrier layer and a material for wound contact comprising at least one hemostat, in particular in granular, powder, flake or short fibrous form. The hemostat is bonded to a carrier material using an adhesive layer between the hemostat and the carrier layer, wherein the adhesive layer and the hemostat are separate layers. The hemostatic material may be selected from chitosan-based products such as chitosan acetate, chitosan lactate, chitosan succinate etc. The hemostatic material is applied as a bandaging material to open wounds in a usual manner.

SUMMARY OF THE INVENTION

In view of the products which were described before or are already on the market, the present invention is directed to a unit for hemostasis and an arrangement containing the same which can be used to effectively stop bleeding in larger wounds, such as gunshot wounds and can be processed in an easy and efficient manner even in complicated situations such as military or civil emergency use.

It is a further object of the present invention to provide a unit for hemostasis which is dimensionally stable and flexible at the same time to improve wound care management in particular of bullet channels.

These objects are achieved by providing a unit for hemostasis, which unit is configured to be directly applied to a bleeding wound and comprises an envelope enclosing an inner space as well as an effective amount of a hemostatic material disposed within the inner space.

That is to say, the unit for hemostasis according to the present invention has a three-dimensional rather than a two-dimensional configuration and, thus, allows a more effective treatment of larger bleeding wounds such as gunshot wounds, for example, can be directly applied to a bullet channel or other wounds received in action.

In a further aspect, the present invention is directed to an arrangement containing two or more units for hemostasis as explained above. Those arrangements contain the units for example arranged in series, in particular in chain-like manner wherein consecutive units are connected to each other. The individual units might be separated from each other by a healthcare professional, for example by hand or a suitable medical device such as bandage scissors.

The present invention is further directed to a method for producing an arrangement of units for hemostasis as described above wherein an effective amount of hemostatic material is disposed within an interior region of a starting material, and wherein neck regions are formed on both sides of the charge so as to form an envelope enclosing the charge.

In a further aspect, the present invention is directed to the use of a hemostatic unit or an arrangement as described above as bandaging material in the military area (military and security products) or as civil emergency bleeding products or as workplace and remote medicine products.

BRIEF DESCRIPTION OF THE DRAWINGS

FIG. 13 A-F shows a test sequence in chronological order for prototype ATR 3.0. The hemostatic unit changes its form during application: the original form is converted to a gelled mass, which subsequently is resorbed by the human body.

The enclosed figures are intended to contribute to a further understanding of the present invention. The figures display exemplary embodiments of the present invention and, taken together with the detailed description, serve to explain principles and concepts of the invention. Other embodiments and many advantages of the invention can be understood based on the drawings. While FIGS. 1-3 show advantageous embodiments of the invention in the form of prototypes along with a centimeter scale for comparison, the elements of the schematic drawings in FIGS. 4-10 are not necessarily drawn to scale.

Figure 1:
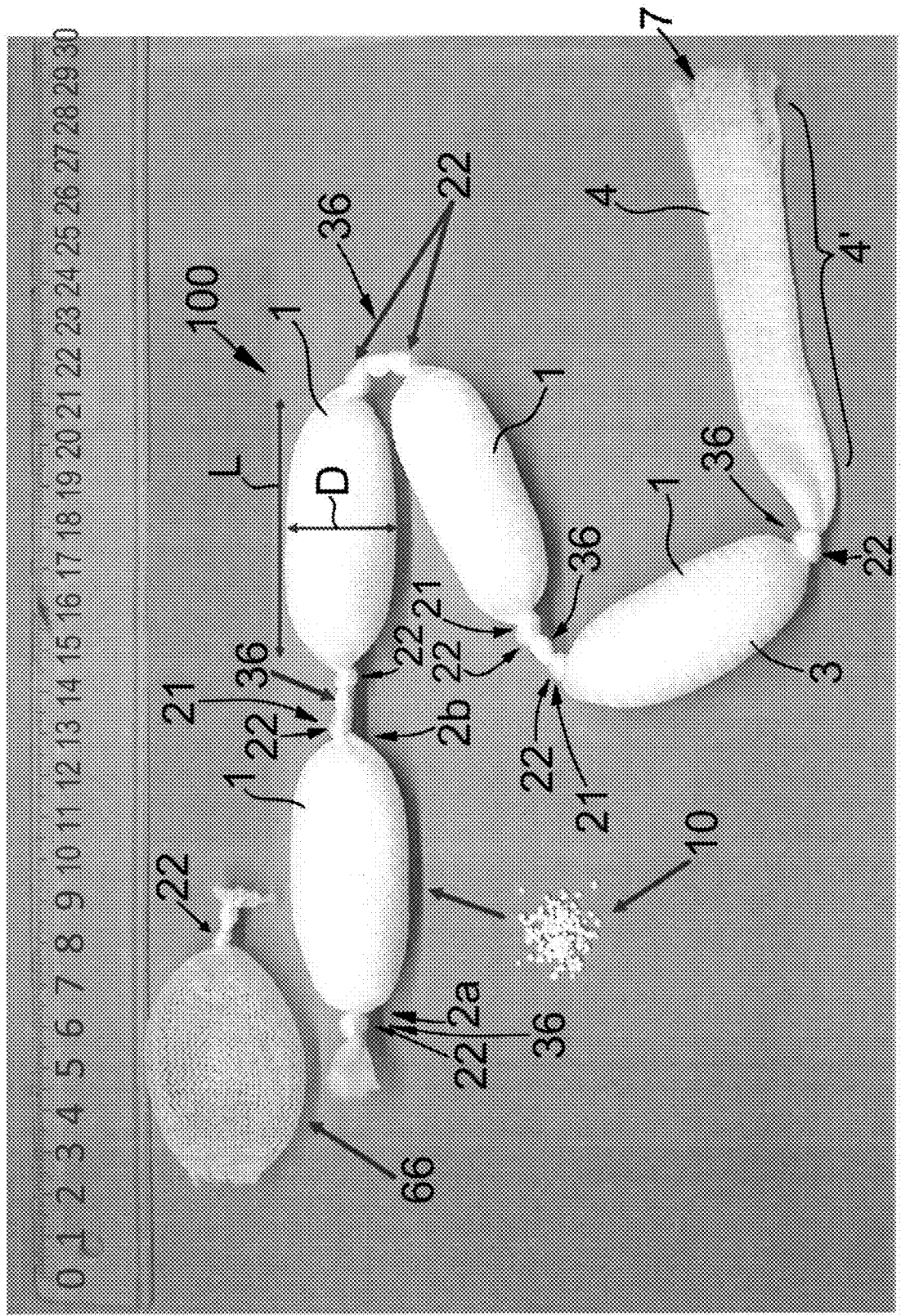
FIG. 1 shows a prototype of an arrangement comprising several units for hemostasis according to an embodiment of the present invention, as well as an exemplary sample of hemostatic material in the form of granules, and an exemplary sample of a piece of a starting material used to form envelopes of the units.

In the figures, elements, features and components which are identical or have the same function or effect have been labelled using the same reference sign, unless indicated otherwise.

DETAILED DESCRIPTION OF THE INVENTION

According to a first aspect, the present invention is directed to a unit for hemostasis, wherein the unit is configured to be directly applied to a bleeding wound and comprises an envelope enclosing an inner space as well as an effective amount of a hemostatic material disposed within the inner space.

In an embodiment, the envelope comprises a reticular material and/or a material formed from fibers. For example, the envelope can be made from a textile, in particular, a knitted fabric, a woven fabric, a braided fabric or a nonwoven fabric.

Alternatively, the envelope might comprise a fleece-type material, a wadding-type material or a foil-type material, in particular a perforated foil or an unperforated foil.

The form of the envelope as such is not restricted as long as it is providing an envelope enclosing an inner space. Therefore, the primary function of the envelope is to provide a three-dimensional structure or coating for the hemostatic material which is bio-degradable and which is disposed in an inner space formed by the envelope. As such, the envelope can be formed from a section of a hose-shaped material and/or is of a bag-type form and/or has an elongate shape.

In a preferred embodiment, the whole unit has a substantially cylindrical shape, in particular a substantially cylindrical shape with rounded ends or is sausage-shaped or egg-shaped or pillow-shaped or substantially spherical.

It is in particular preferred if the envelope material has a net-like form since this will allow blood and other body fluids to enter the unit and to come into contact with the hemostatic material more rapidly and more easily. This will prevent forming of an external layer, for example, of an envelope material, which may in particular be bio-degradable, and blood or blood components, and will allow bringing the same effectively into contact with the hemostatic material.

In a preferred embodiment, the envelope of the unit for hemostasis at least is closed at one end of the unit, preferably at both ends thereof, by a knot, a weld, a seam, a staple/clip or adhesive bonding. Combinations of at least some of the aforementioned ways of closing the envelope are also conceivable. In a preferred embodiment, the unit is closed at both ends, where the closing forms a junction to the next unit thus forming an arrangement of two or more units for hemostasis.

The dimension of the unit according to the present invention is not limited. However, it is preferred that the length of the unit is approximately between 0.5 and 30 cm and/or that the outer diameter or width of the unit is between approximately 0.5 and 20 cm. In some developments of the invention, the length of the unit may for example be between approximately 1 cm and approximately 20 cm, and/or the outer diameter or width of the unit may for example be between about 0.5 and 15 cm. The unit more preferably is having a length of about 6 cm and/or a diameter of approximately 3 cm. Basically, the unit should have a preferred length of 5-10, preferably 5-7 cm and a preferred diameter of 1-4, preferred 2-3 cm.

An exemplary unit 1 for hemostasis is shown in FIG. 1 where the dimensions of a single unit 1 (not including the end sections) are about 6 cm×2.5 cm, i.e. L≈6 cm and D≈2.5 cm. In this embodiment the end sections are formed by knots, which, however, can be replaced by sections obtained by welding, sewing, clipping, stapling or gluing together.

The size of the unit preferably is such that it can be used to close a bullet entry wound as it can appear in the military field. Furthermore, the unit for hemostasis may be adapted in size to stab wounds and will have a somewhat smaller dimension then. The skilled person will be able to determine the ideal dimensions of the unit for hemostasis which can be used for a given medical/surgical application.

In case of larger wounds than those disclosed above, such as wounds resulting from car accidents or shrapnels, the unit for hemostasis according to the present invention may be used in a larger number in order to provide hemostasis.

In practice, it turned out that a single unit having the size of about 6 cm×2.5 cm is preferred since it can be used for a large number of different injuries and can be easily handled.

In accordance with a development of the invention, the envelope may entirely or partially be biodegradable and/or bioresorbable. The term biodegradable means that a material is susceptible of breakdown into simpler components by biological processes, such as by enzymatic action. The term bioresorbable means that the material can be broken down by the body and do not require mechanical removal, such as it is the case with sutures.

In a preferred embodiment, the entire unit for hemo stasis according to the invention is biodegradable and/or bioresorbable. That is to say, both the envelope material and the hemostatic material are biodegradable and/or bioresorbable. This is highly advantageous since the hemostatic unit of the invention may be left in the place where it has been applied to (wound channel etc.) without any need for subsequent removal. The unit for hemostasis is totally resorbed by the human or animal patient's body within a very short time, i.e. is totally resorbed after a maximum of 7-10 days, preferably 2-3 days after application.

A preferred example of an envelope material 4 for forming the envelope 3 is shown in FIG. 1, i.e. a fast-soluble polymer PVA mesh.

Alternatively, in other developments of the invention, the envelope may not be biodegradable.

For example, the envelope may comprise a biodegradable polymeric material or may comprise a non-biodegradable polymeric material or may comprise at least one biodegradable polymeric material and at least one non-biodegradable polymeric material.

The envelope may in some embodiments of the invention comprise a synthetic material or a natural material or a combination of at least one synthetic material and at least one natural material. In particular, the synthetic material may be a synthetic polymeric material and/or the natural material may be a natural polymeric material. The synthetic material or the natural material, or each of them, may in particular be a fiber-forming material.

For example, in embodiments of the invention in which the envelope comprises a reticular material and/or a material formed from fibers, the fibers or yarns used may be made from the synthetic or natural material.

In some embodiments of the invention, the envelope may be made from a reticular material or mesh-type material and/or a material formed from fibers and may contain bio-degradable or non-biodegradable fibers or yarns, or a combination of both biodegradable and non-biodegradable fibers or yarns, which are combined in the reticular, mesh-type or fibrous material of the envelope. A combination of biodegradable and non-biodegradable fibers or yarns may be provided by including, in the material used for the envelope, discrete fibers or yarns that will dissolve, in combination with other fibers or yarns that will not dissolve.

A reticular or mesh-type envelope material is preferred since it will allow the body fluid to enter the unit for hemostasis more easily and faster and thus, will lead to faster hemostasis. In this case, it is important to keep a defined ratio of the mesh or pore size of the envelope material and the particle size of the hemostatic material. In order to ensure that the particles forming the hemostatic material may not emerge from the unit, the average mesh/pore size should not be larger than the average particle size; preferably the average particle size to average mesh/pore size ratio should be about 1:0.9 to 1:0.1. Although it is acceptable that a certain small amount of the particles forming the hemostatic material emerges from the unit, this amount should be kept as low as possible.

In embodiments in which the envelope contains non-biodegradable or non-bioresorbable fibers, e.g. in the form of a non-biodegradable mesh, the blood flow may be stopped in the emergency situation with the aid of the hemostatic material released by the mesh while forming a gel in contact with blood, while the mesh may be removed later.

In embodiments in which an entirely or partially biodegradable or bioresorbable envelope is provided, the envelope preferably comprises a polymeric material which is rapidly dissolving in aqueous solutions, such as polyvinyl alcohol (PVA), polylactic acid, starch or mixtures thereof. Of course, the requirements for all these polymeric materials are the same in these embodiments, i.e. the polymeric materials must be biodegradable and ideally bioresorbable. Other materials, which might be used as biodegradable or bioresorbable materials in the context of the present invention for the envelope could be selected from oxidized cellulose, collagen, polycaprolactone, chitin and others, just to name a few. Polyvinylalcohol (PVA) is particularly preferred.

If the envelope comprises a natural polymeric material, the natural polymeric material may in particular be selected from cotton, natural silk, starch, cellulose, chitosan or mixtures thereof. If, in addition thereto or alternatively, the envelope comprises a synthetic polymeric material, the synthetic polymeric material may in particular be selected from polyethylene, polypropylene, polyurethane, polyether ether ketone, polyethylene terephthalate, and others, or mixtures thereof.

As noted above, the hemostatic material (10) preferably is biodegradable and/or bioresorbable.

The hemostatic material (10) may be selected from native or modified starch, oxidized cellulose, chitosan, collagen (gelatine) or mixtures thereof.

Modified starch is preferably selected from carboxyalkyl starch, for example carboxy-n-alkyl starch or carboxy-iso-alkyl starch. Preferred examples of carboxy-n-alkyl starch are carboxymethyl, carboxyethyl, carboxypropyl or carboxybutyl starch.

Modified starches such as the above preferred examples are a preferred hemostatic material since they allow rapid soaking of liquid blood components (due to their hydrophilicity) and gelling, are 100% resorbable by the human body and biodegradable so that no post-surgery removal of the hemostatic material is required. Furthermore, starch products are well-tolerated by the human body and do not cause allergic reactions. Most preferred is carboxymethyl starch made from potato starch.

As a native starch, starch from potato, sweet potato, rice, rye, barley, oat, millet, soft wheat, hard wheat, corn, sorghum, manioc, tapioca, arrowroot, bean, lentil, wrinkled pea, round pea, yam, taro, mango or banana starch or combinations of the mentioned can be used.

Preferably, the hemostatic material used in the unit for hemostasis is in the form of powder, granules, pellets, cylindrical pieces or shreds. An average size of the particles or pieces of the hemostatic material, e.g. an average diameter, may be between about 0.1 mm and about 30 mm.

The hemostatic material preferably is a gel-forming material which provides good adhesiveness to the wound/tissue and thus improves hemostasis and forms a protective layer on the wound/tissue. An example of such a material are the above mentioned modified starch materials.

The hemostatic unit thus may change its form during application: the original form is converted to a gelled mass, which subsequently is resorbed by the human body.

Should granules be used for the hemostatic material, they can have a solid or porous form and have an average diameter of about 0.1-30 mm, more preferably of about 0.2-7 mm. A most preferred average diameter is from about 1-2 mm, or 1-1.6 mm. Preferably, about 80% of the particles have a diameter within a range of ±20% of the average diameter. The diameter of a particle can be determined by a microscopic method, for example by applying Martin's diameter, however, separation methods or method determining the specific surface area may also be used to determine the average diameter.

For example, a method of determining the average diameter and/or the particle size distribution of the particles or granules is the application of separation methods, in particular by sieving (use of a sieve shaker; for example Retsch® Vibratory Sieve Shaker AS 200 basic). It is generally referred to the methods and devices described in *Remington, The Science and Practice of Pharmacy, 22$^{nd}$ edition, chapter 38.*

In a variant, the hemostatic material in the unit for hemostasis may be in the form of a single, preferably porous, pellet or tab, or may be in the form of a small number of such pellets or tabs. In such variants, a pellet or tab may be relatively large, and may for example be up to about 30 mm in diameter or in length. Such pellets or tabs may, for example, each have a spherical, cuboid-like, egg-like or substantially cylindrical shape. Single pellets or tabs may each be enclosed individually by the respective envelope to form units for hemostasis. The pellet or tab may e.g. be formed by compression.

Preferably, porous particles or granules are used as hemostatic material. They have the clear advantage of providing improved absorption of liquids such as blood due to their inherent capillary forces. The porosity of the particles should be larger than about 50%, and the maximum value should not exceed 90% (i.e. 50-90%). A preferred range of the porosity is 70-85%, most preferred 75-80%. The high porosity guarantees a rapid and complete ingress of liquids into the unit's body and thus leads to a faster hemostasis.

The porosity can be measured by applying the following formula:

Porosity=1−(absolute density/bulk density)

The absolute density of the granules/particles can be determined by using a gas displacement pycnometry system (for example AccuPyc® series produced by Micromeritics).

The bulk density of the granules/particles can be determined by standard procedures described in *Remington, The Science and Practice of Pharmacy,* 22nd edition, chapter 38: The bulk density is defined as the ratio of powder bed mass to volume of that powder bed, including both the pores and gap volume. The powder is filled into a cylinder and, after gentle tapping or vibration for a given period and intensity, the volume of powder bed is measured directly from the cylinder. The bulk density then is calculated from the ratio of powder weight to volume.

In a further preferred embodiment, the filling grade of the unit is set to a specific degree. The filling grade of the unit is defined as the volume ratio between the actual loading of the hemostatic material within the inner space and the maximum loading expressed in volume percent. Each given envelope of the unit will have a maximum inner space volume for filling the hemostatic material. For the above calculation, it is defined that the maximum volume is achieved by filling the hemostatic material into the inner space without applying external forces such as pressure. The maximum load the envelope may accommodate thus defines the maximum volume of the inner space and the maximum volume of the hemostatic material.

An ideal filling grade according to the invention is about 50-90, preferably 60-70 Vol %. If the filling grade is below 50 Vol. %, the handling of the unit will be difficult since it does not possess the required dimensional stability. If the filling grade exceeds 90%, the unit will lose flexibility and will tend to have a too high stiffness. For the envisioned application of the unit for hemostasis, for example in closing a bullet entry wound, an ideal balance between dimensional stability and flexibility is required for optimum handling of the surgeon. This is achieved by the above preferred filling grades.

A preferred embodiment of a unit for hemostasis of the present invention comprises a biodegradable and/or bioresorbable, reticular or mesh-type envelope material, a biodegradable and/or bioresorbable hemostatic material forming a gel after contact with liquids, where the hemostatic material is in the form of particles or granules having an average diameter of about 0.5-2 mm and a porosity of about 70-85%. The unit preferably has a filling grade of about 60-90 Vol % and the ratio of the average particle size of the hemostatic material, to the average mesh/pore size of the envelope material should be about 1:0.9 to 1:0.1. The dimensions of the unit preferably are about 10 cm×2.0 cm, preferred about 6 cm×3 cm of a "sausage-type" form or of egg-form having similar dimensions, where the unit is closed at two ends. The preferred hemostatic material is modified potato starch and the preferred envelope material is a PVA mesh. The unit may be provided as a chain or assembly.

By combining these parameters, some advantageous effects may be achieved: due to the ratio of mesh to particle size, the particles forming the hemostatic material may not emerge from the unit. Furthermore, the porosity and size of the particles allows a rapid ingress of body fluids, immediate gel-forming and, as a consequence, rapid hemostasis. The specific filling grade leads to a three-dimensional shape of the unit which, one the one hand, provides dimensional stability and, on the other hand, still provides some flexibility to the unit. Thus this preferred unit is ideal for wound management of bullet channel wounds since the surgeon/ ambulance men may easily insert the unit into the wound channel and rearrange it within the bullet channel as required.

In a further embodiment of the invention, an arrangement of two or more units for hemostasis as described above is provided, wherein the units are coupled to each other. Preferably, the units are arranged in series, in particular, in a chain-like manner, where consecutive units are connected to each other.

This arrangement will allow for an easy handling of the arrangement in practice, for example in military applications in the field, where easy handling and a flexible adaption to a given situation is required. For example, a longer chain of units for hemostasis might be divided in single units, where smaller wounds have to be treated. Whenever the situation requires hemostasis of heavily bleeding wounds or the treatment of wide areal bleedings, two, three or more of the single units can be arranged as a closed area wound cover (see FIG. 9) and be used at one time to speed up the wound care process.

In an embodiment, the envelopes of the units forming the arrangements are formed in one piece with each other, in particular, from a hose-type starting material. Preferably, the arrangement is partitioned for forming several units by a neck region or several neck regions, wherein the inner spaces of consecutive units are separated from each other by the neck region or one of the neck regions. As such, it is preferred that the envelope of each of two consecutive units is closed in the area where the envelope transitions into the neck region, by a knot, a weld, a seam, a staple/clip or adhesive bonding. Thus, the arrangement is configured such that the units are separable from each other, preferably separable from each other by a user by hand or by a suitable medical device.

In a preferred embodiment, a predetermined breaking point is provided between adjacent units. Such a predetermined breaking point might be formed by a perforation, or by a transition within the material of the envelope, from a reticular type material or a material made from fibers to a foil-type material, or by a weakened region of textile in the area of the predetermined breaking point.

Preferably, the arrangement comprises a number of units ranging from two units to about twenty units, preferably a number of five or six units.

It is also conceivable that the arrangement contains the same or different units, i.e. units having a different size and/or shape within one single arrangement. However, in the usual case, the arrangement will comprise units having essentially the same size and/or shape.

Furthermore, the present invention is directed to a method for producing an arrangement of units for hemostasis as described above, wherein an effective amount of hemostatic material is disposed within an interior region of a starting material, and neck regions are formed on both sides of the charge so as to form an envelope enclosing the charge.

Figure 4:
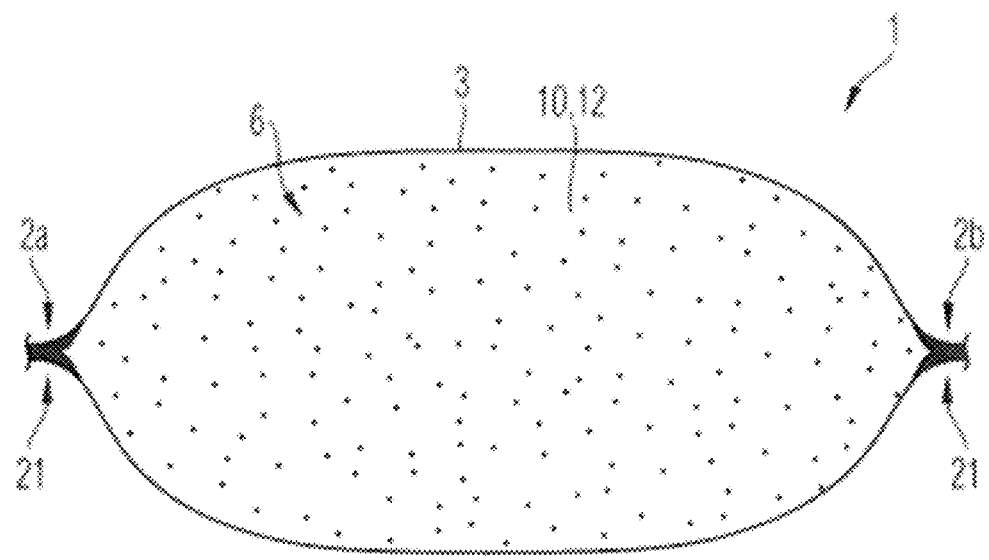
FIG. 4 illustrates a single unit for hemostasis according to an embodiment of the present invention, in a schematic sectional view, taken along a longitudinal axis of the unit.

A schematic view of a longitudinal cross-section of a unit 1 for hemostasis is displayed in FIG. 4. The sausage-shaped unit 1 of FIG. 4 comprises a charge 12 of an effective amount of a hemostatic material 10, which is in the form of granules, not shown in any more detail in FIG. 4, and which is enclosed by an envelope 3 which, in this example, is a biodegradable envelope 3. In this manner, the hemostatic material 10 is disposed within an inner space 6 of the unit 1. The envelope 3 is closed at both ends 2a, 2b of the unit 1. Hence, the hemostatic material 10 is securely held together and cannot escape from the inner space 6 enclosed by the envelope 3. In other words, the envelope 3 is sufficiently closed to keep the hemostatic material 10 inside the inner space 6.

In FIG. 4, the unit 1 has substantially a shape that is similar to the shape of a relatively straight, unbent sausage. Other suitable outer shapes for the unit 1 are displayed in exemplary manner in FIG. 5 (a) to FIG. 5 (e). In all examples of FIG. 5 (a)-(e), the envelope 3 is closed at ends 2a, 2b of the unit 1.

Figure 5:
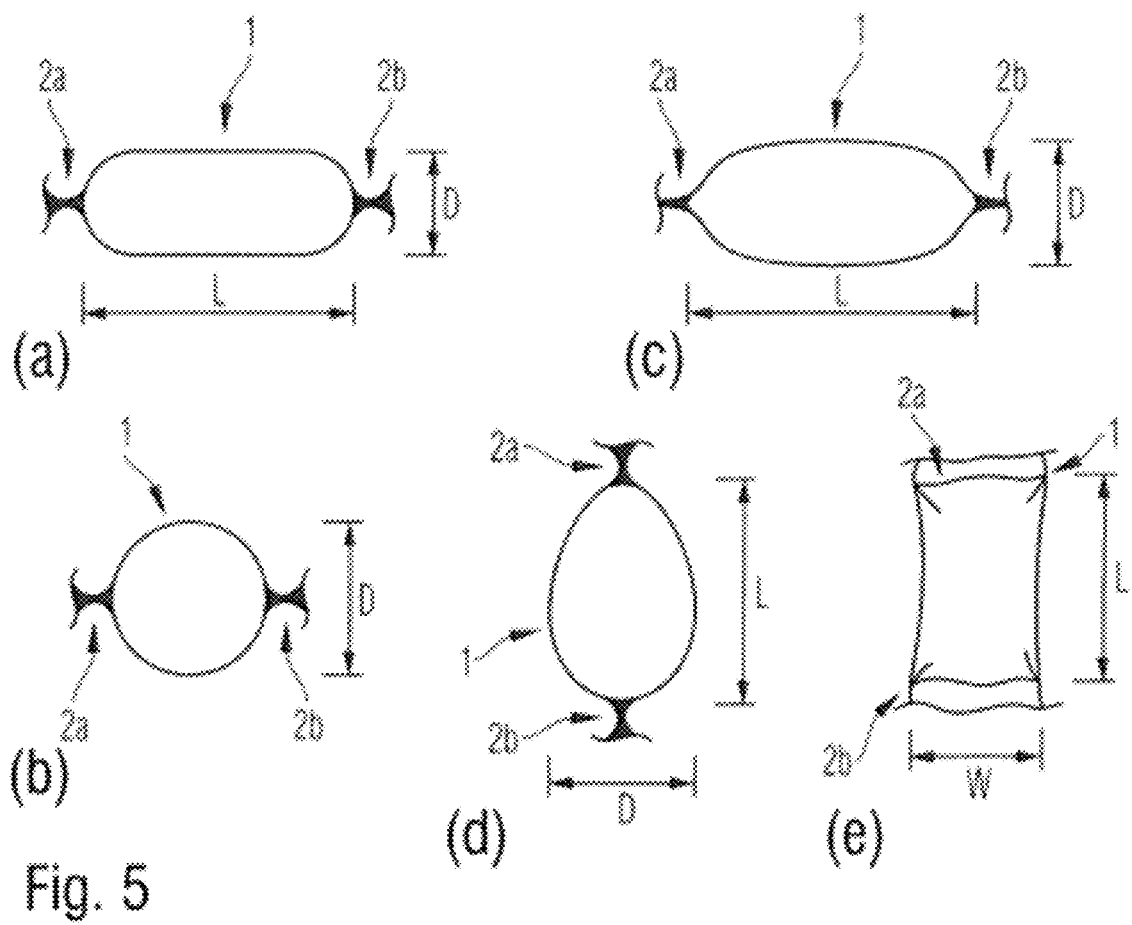
FIG. 5 schematically illustrates units for hemostasis having various shapes, in accordance with embodiments of the present invention.

A sausage-shaped unit 1 is shown in a side view in FIG. 5 (c), the unit 1 of FIG. 5 (c) being similar in shape to the unit 1 of the embodiment of FIG. 4.

In FIG. 5 (a), a unit 1 according to another embodiment is displayed in side view which has a cylindrical outer shape with rounded end portions at each end 2a, 2b, wherein the end portions have shapes that are similar to semi-spheres.

In FIG. 5 (b), a unit 1 according to a further embodiment is displayed which is spherical, i. e. is shaped substantially as a sphere. Ends 2a, 2b are defined in this case as regions on diametrically opposed sides of the sphere where the envelope 3 is closed.

Further, in FIG. 5 (d), in accordance with another embodiment, a unit 1 is schematically displayed in side view which is egg-shaped. Hence, the outer shape of the envelope 3 of the unit 1 of FIG. 5 (d) has a larger radius of curvature close to the second end 2b compared to the radius of curvature close to the first end 2a. Accordingly, the unit 1 of FIG. 5 (d) is more pointed at the end 2a, being the upper end of the unit 1 in FIG. 5 (d).

Moreover, FIG. 5 (e) displays a schematic plan view of a unit 1 in accordance with a further exemplary embodiment, wherein the unit 1 is shaped like a pillow. While the unit shapes of FIGS. 4 as well as 5 (a), (b), (c) and (d) are rotationally symmetric shapes, the pillow-shape of FIG. 5 (e) is a shape having corners. At the first and second ends 2a and 2b of the unit 1 of FIG. 5 (e), the pillow-shaped unit 1 may be coupled to adjacent units 1, which may have the same shape and are not displayed in FIG. 5 (e), along approximately the entire length of the edges of the pillow shape at the end 2a and 2b, respectively.

In each of the FIGS. 5 (a) to 5 (e), the length L of the unit 1 may be in the range of about 0.5 cm to 30 cm, while the diameter D may be in the range of about 0.5 cm to 20 cm. Moreover, while a length L of the pillow-shaped unit 1 of FIG. 5 (e) may be in the range of about 0.5 to 30 cm, a width W of the unit 1 may be between about 0.5 and 20 cm.

Figure 2:
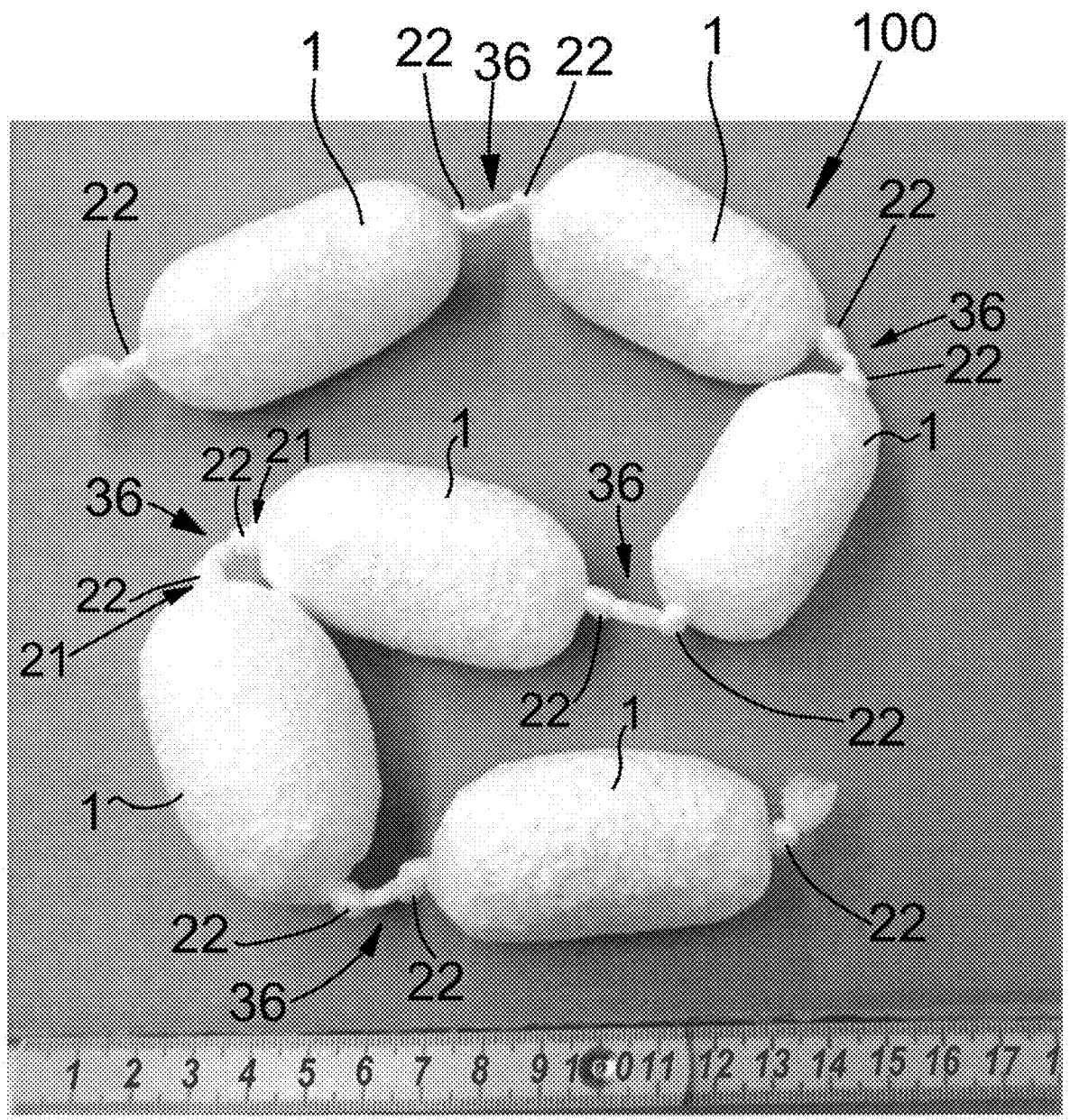
FIG. 2 shows another prototype of an arrangement comprising several units for hemostasis according to a further embodiment of the present invention.
Figure 3:
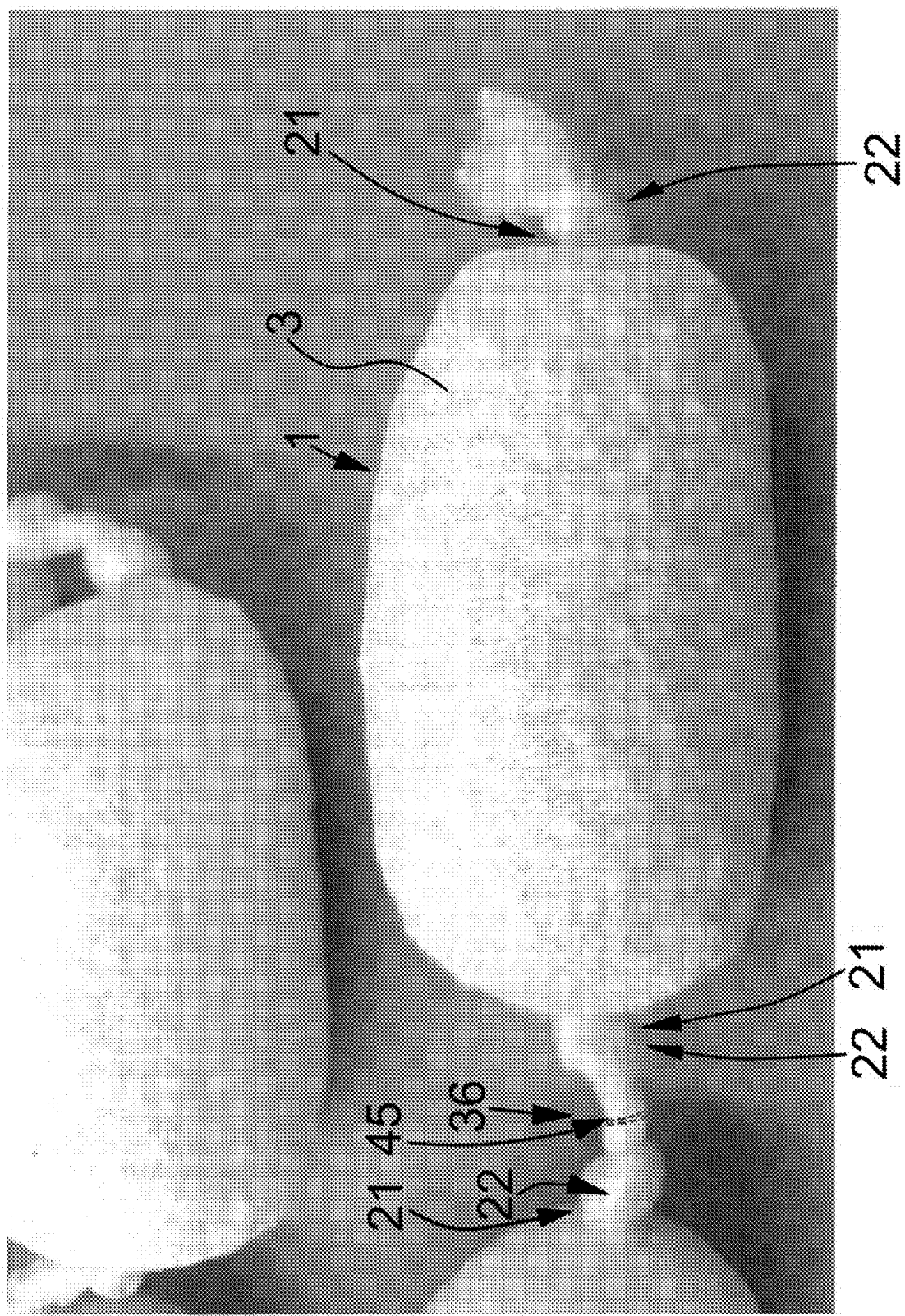
FIG. 3 shows two units of the arrangement of FIG. 2 in a close-up view.

Arrangements 100 of units 1 for hemostasis according to embodiments of the present invention are displayed in FIGS. 1 to 3. The units 1 of FIGS. 1 to 3 are configured to be directly applied to a wound and are each formed in a manner analogous to the construction schematically illustrated in FIG. 4, comprising an envelope 3, an inner space 6 and a hemostatic material 10 disposed within the inner space 6. The envelope 3 of each of the units 1 in FIGS. 1 to 3 may be formed so as to be biodegradable entirely or at least in part, or may not be biodegradable.

The arrangement 100 of FIG. 1 comprises four units 1 for hemostasis, while the arrangement 100 of FIGS. 2-3 comprises six units 1. Also shown is in FIG. 1 a remaining portion 4' of a starting material 4 that has been used for forming an envelope 3 of the units 1. During the production of the arrangement 100, the remaining portion 4' may be used to form a further unit 1 or may be cut.

The arrangement 100 of FIG. 1 can be produced by disposing an effective amount of the hemostatic material 10 in the form of a charge 12 (see FIG. 4) inside the hose-shaped starting material 4, i.e. within an interior region 7 of the starting material 4. Then, neck regions 36 are formed on both sides of the charge 12, whereby the envelope 3, closed on opposite sides of the charge 12, is formed. The charge 12 is hence enclosed by the envelope 3 so as to form a unit 1 for hemostasis closed at first and second ends 2a, 2b. Then, a further charge 12 of hemostatic material 10 is filled in the interior space 7 of the starting material 4, and a further neck region 36 is formed.

In this manner, by alternately repeating the steps of filling or disposing a chosen, effective amount of hemostatic material 10 inside the inner space 7 of the hose- or sleeve-type starting material 4, and forming a neck region 36, an arrangement 100 as displayed in FIG. 1 can be obtained in which the units 1 are coupled to each other in series in a chain-like manner. The coupling of the units 1 is obtained by using the starting material 4, being of sufficient length, to form several envelopes 3 for several units 1 in one piece with each other by providing the neck regions 36. Consecutive units 1 are therefore, in the arrangement 100 of FIG. 1, connected to each other by the envelopes 3 being formed in one piece with each other.

The arrangement 100 of FIGS. 1-3 is thus partitioned, for forming several units 1 for hemostasis, by several neck regions 36. The inner spaces 6 of consecutive units 1 are separated from each other by the corresponding neck region 36 between these units 1. The envelopes 3 of the units 1 therefore form connected three-dimensional bag-type sections containing the hemostatic material 10.

In FIG. 1, the starting material 4 from which the envelope 3 has been formed is an elongate, hose- or sleeve-shaped, mesh-type or reticular material, in this example a PVA mesh to form a biodegradable envelope 3. The mesh of the starting material 4 is formed as a finely knitted fabric of suitable yarns each composed in turn of individual filaments. A sample 66 of starting material 4 without hemostatic material 10 disposed inside is displayed in FIG. 1 as well, one end of the sample being closed by a knot 22 in exemplary manner.

An arrangement 100 in accordance with a further embodiment, similar to the embodiment of FIG. 1, is shown in FIGS. 2 and 3. The explanations given above with regard to FIG. 1 apply to FIGS. 2 and 3 in analogous manner. In each of FIGS. 1 and 2, in order to illustrate the sizes of the arrangements 100 and units 1 in accordance with these exemplary embodiments, a ruler comprising a centimeter scale is displayed for comparison. Even though the dimensions illustrated in FIGS. 1 and 2, with the outer diameter D of the unit 1 in FIG. 1 being approximately equal to 2.5-3.0 centimeters and the length L of the unit 1 in FIG. 1 being approximately equal to 6 centimeters, are preferred, the sizes of the units 1 may be chosen in many different ways. In particular, in accordance with variations of these embodiments, the length L of each unit 1 in FIGS. 1-3 may be between approximately 0.5 cm and approximately 30 cm and/or the outer diameter D of the unit 1 may be between approximately 0.5 cm and approximately 20 cm.

FIGS. 1 to 3 also show that in the embodiments displayed in these figures, the envelope 3 of each unit 1 is closed at both ends 2a, 2b of the respective unit 1 by a knot 22, in an area 21 where the envelope 3 transitions into the neck region 36. In other words, each neck region 36 is formed in FIGS. 1 to 3 by forming two consecutive knots 22 with a small distance between them. By forming the neck regions 36 using knots 22, envelopes 3 formed from a starting material 4 that is hose-shaped or sleeve-shaped can be reliably closed.

However, in accordance with further embodiments displayed in schematic manner in FIGS. 6A to 6E, the envelope 3 of each of two consecutive units 1 may be closed in the area 21 in other ways, in order to form the neck region 36 between subsequent units 1.

Figure 6A:
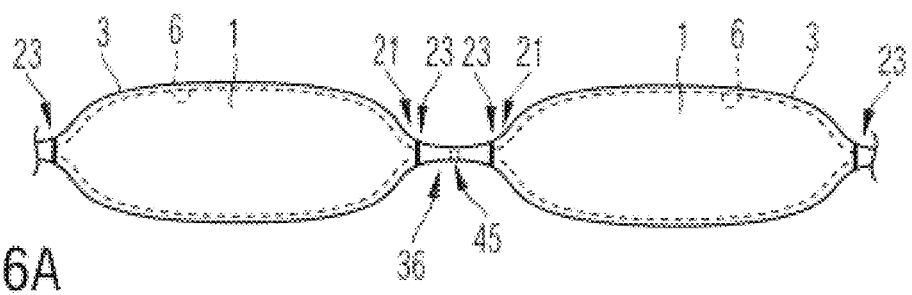
FIG. 6A-6E schematically show exemplary ways of closing envelopes of units for hemostasis in a neck region between two adjacent units according to embodiments of the present invention.

For example, in the embodiment of FIG. 6A, the envelope 3 can be closed by forming welds 23 in the areas 21 where the envelope 3 of consecutive units 1 transitions into the neck region 36 separating these units 1. In this way, the production of the units 1 for hemostasis and of an arrangement 100 comprising several of such units 1 can be simplified.

Figure 6B:
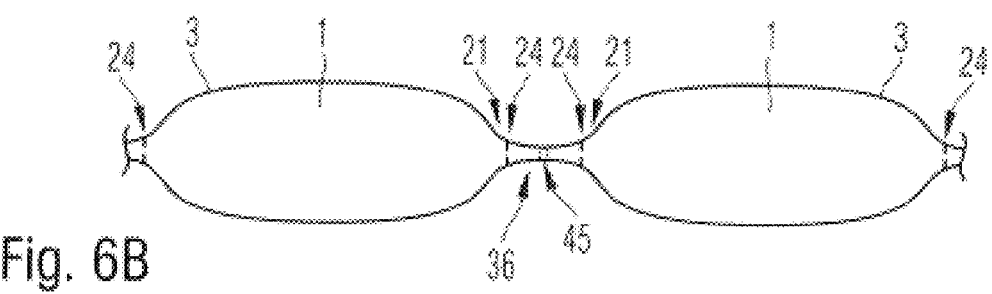

In accordance with a further embodiment schematically displayed in FIG. 6B, the envelopes 3 may be closed in the areas 21 by seams 24, which may be implemented using a suitable sewing thread.

Figure 6C:
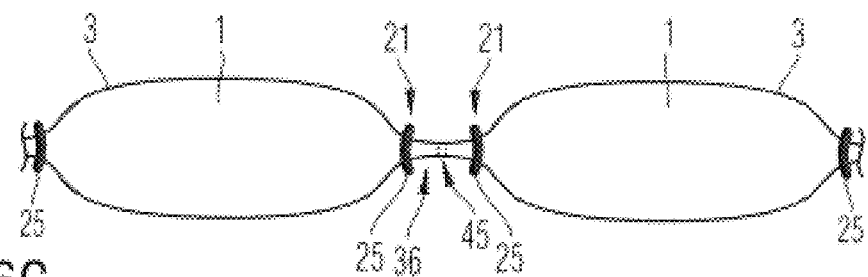

In accordance with another embodiment schematically displayed in FIG. 6C, the envelopes 3 may be closed in the areas 21 by clips 25, firmly clasping a portion of the starting material 4 from which the envelope 3 is formed in the circumferential direction thereof.

Figure 6D:
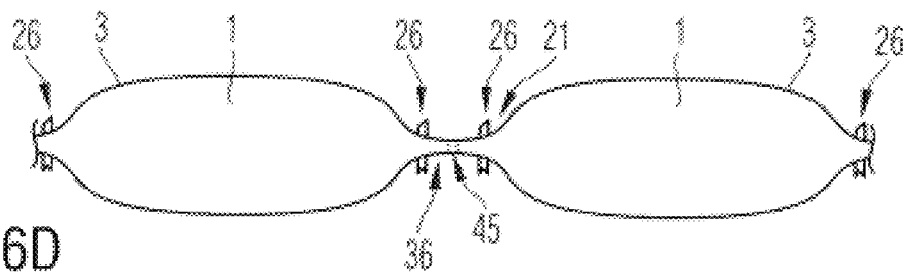

Moreover, in accordance with another embodiment schematically displayed in FIG. 6D, staples 26 may be used to close the envelopes 3 in the areas 21, wherein the staples 26 may locally penetrate the starting material 4.

Figure 6E:
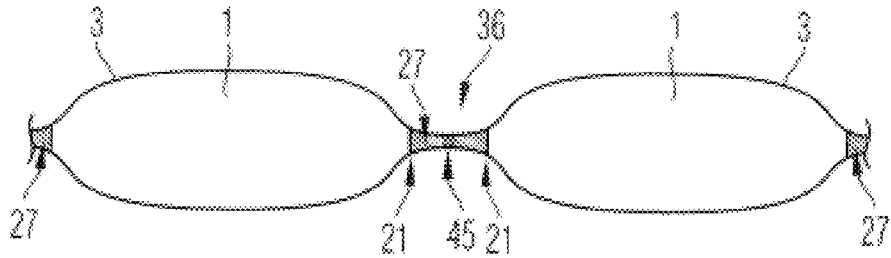

In accordance with a still further embodiment displayed in FIG. 6E, closing the envelopes 3 in the areas 21 may be accomplished using a suitable adhesive applied to the starting material 4 in an adhesive bonding region 27 which, in the example of FIG. 6E, extends along the entire neck region 36, but may in variations of this embodiment be confined to local areas of the neck region 36 instead.

The ways of closing the envelope 3 as displayed in FIGS. 1-3 and 6A-6E may also be used in case the units 1 are to be provided individually as single units 1 instead of being coupled to each other in an arrangement 100.

In order to be able to easily separate one or more units 1 from an arrangement 100 containing, for example, between two and twenty units 1 or between two to ten units 1, for example five units 1, or six units 1 as shown in FIG. 2, a predetermined breaking point 45 is provided between consecutive adjacent units 1, see FIGS. 6A-6E. In this manner, the units 1 are separable from each other by a user by hand, which may contribute to a simple and rapid handling and use of the units 1 in critical situations. The user can choose the number of units 1 to be used for application to a given wound and simply separate the chosen number from the arrangement 100.

Figure 7A:
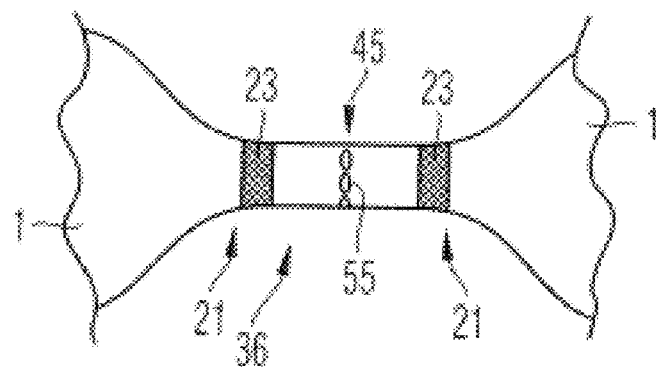
FIG. 7A-7C schematically illustrate ways of implementing a predetermined breaking point between adjacent units for hemostasis in arrangements according to embodiments of the present invention.
Figure 7B:
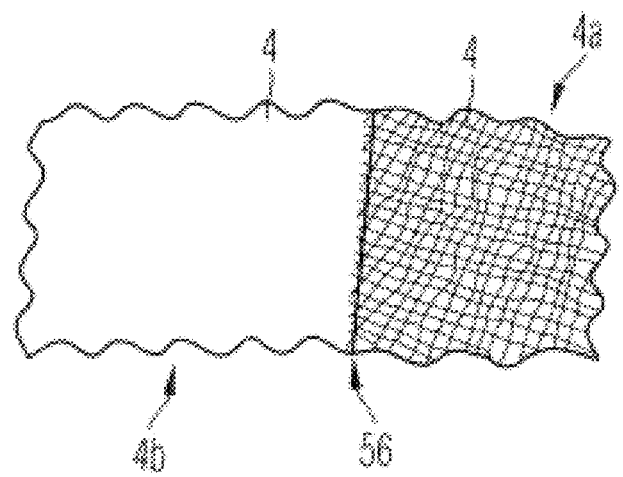
Figure 7C:
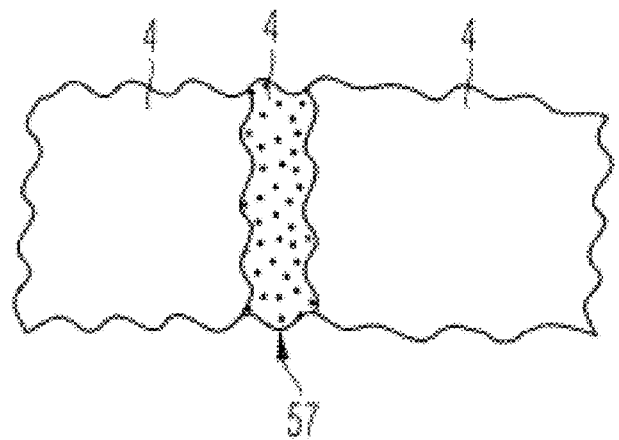

FIGS. 7A to 7C show how the breaking point 45 or 57, respectively, can be implemented in exemplary embodiments of the present invention.

In FIG. 7A, two units 1 for hemostasis, connected in an arrangement 100 and not shown in their entirety in this figure, are coupled in the neck region 36, as described before, and the envelopes 3 of each of these units 1 are closed by welds 23. However, closing the envelopes 3 may be done in another way, for example as described with reference to FIGS. 6A-6E above. Approximately at the center of the neck region 36, between the welds 23, a perforation 55 is provided to implement a predetermined breaking point 45. At the breaking point 45, the units 1 may be torn apart by hand.

FIG. 7B shows, in schematic manner, that the breaking point 45 may also be formed, in accordance with other embodiments, by a transition 56 from a reticular-type material 4a or a material made from fibers to a continuous, foil-type material 4b, within the starting material 4 used to form the envelopes 3.

Furthermore, FIG. 7C schematically illustrates that in accordance with another embodiment, the breaking point 45 may be implemented by a weakened region 57, e.g. within a textile starting material 4, that is provided in the area of the predetermined breaking point 45 before the envelopes 3 are formed.

The three-dimensional shape of the units 1 may be advantageous when one or several of the units 1 are used to staunch bleeding in a severe, strongly bleeding wound, e.g. on the battlefield. The amount, e.g. in terms of volume or weight, of the hemostatic material 10 is comparatively large in relation to the outer enveloping surface area of the unit 1, which means that a quite large amount of hemostatic material 10 may be applied to the wound using a rather compact unit 1.

For example, in the case of the sausage-shaped units 1 of the arrangements 100 as displayed in FIGS. 1-3, having a length L of about 6 cm and an outer diameter D of about 2.5-3.0 cm, the ratio $R=V/A$ of the volume V of the inner space 6 available for receiving the hemostatic material 10 and the outer enveloping surface area A of the unit 1 is approximately in the range between 0.5 $cm^3/cm^2$ and 0.6 $cm^3/cm^2$. Therefore, the sausage-shaped unit 1 e.g. of FIGS. 1-3 has an improved capability of rapidly absorbing large quantities of liquid. A value for R within a range between about 0.4 $cm^3/cm^2$ and about 0.7 $cm^3/cm^2$ is preferred. The other shapes of the units 1 illustrated in FIGS. 5 (a)-(e) also result in a unit 1 for hemostasis that is three-dimensional, with a relatively large ratio R.

In the embodiments of FIGS. 1-3, the charge 12 for a single unit 1 may correspond to approximately 12-16 grams of hemostatic material 10. The hemostatic material 10 is in the form of granules, and a sample of solid granules having an exemplary average diameter of between 1.0 and 2.0 mm is shown in FIG. 1 as well. A preferred range for the average diameter of the granules may be about 1.0 mm to 1.6 mm.

In the case of such a charge 12 of 12-16 grams of rather solid granules of hemostatic material 10, at an average diameter of the granules of about 1.6 mm, the total surface of the hemostatic material 10 may, for example, be in the range between approximately 1200 $cm^2$ and approximately 1600 $cm^2$. In this case, a sausage-shaped unit 1 such as the unit 1 of FIG. 1, of L≈6 cm and D≈3 cm, may exhibit a ratio of the total surface area of the hemostatic material 10 to the outer enveloping surface area A of the unit 1 of approximately 17:1 to approximately 23:1, depending on the weight of a single charge and the average diameter of the granules.

Figure 8:
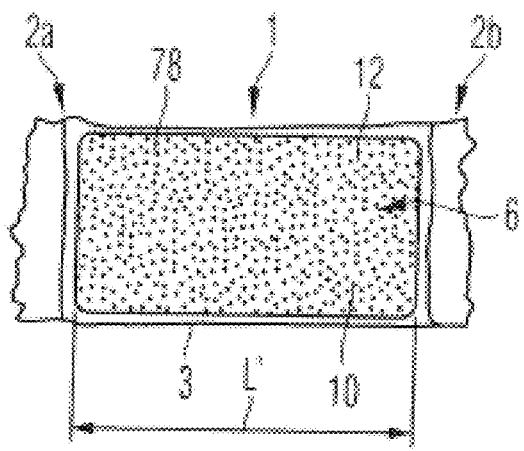
FIG. 8 schematically illustrates a unit for hemostasis in accordance with a further embodiment of the invention, wherein the hemostatic material is in the form of a single pellet or tab.

In a further embodiment of the present invention, a unit 1, which may be a single unit 1 or may be integrated into an arrangement of units for hemostasis, comprises an effective amount of hemostatic material 10 which is provided in the form of a single pellet or tab 78 disposed within an inner space 6 of an envelope 3, whereby the envelope 3 encloses the pellet or tab 78. A schematic sectional view of a unit 1 according to such an embodiment is illustrated in FIG. 8. In FIG. 8, the unit 1 has a pillow-type shape, similar to the unit shown in FIG. 5 (*e*), while the tab 78 has a cuboid-like shape with rounded corners. In variants of this embodiment, the tab 78 may have a spherical shape or a substantially cylindrical shape or an egg-like shape, but other three-dimensional shapes of the tab or pellet 78 are conceivable as well. The tab 78 may, for example, have a length L' of up to or equal to about 30 mm, but other dimensions are conceivable, too.

Figure 9:
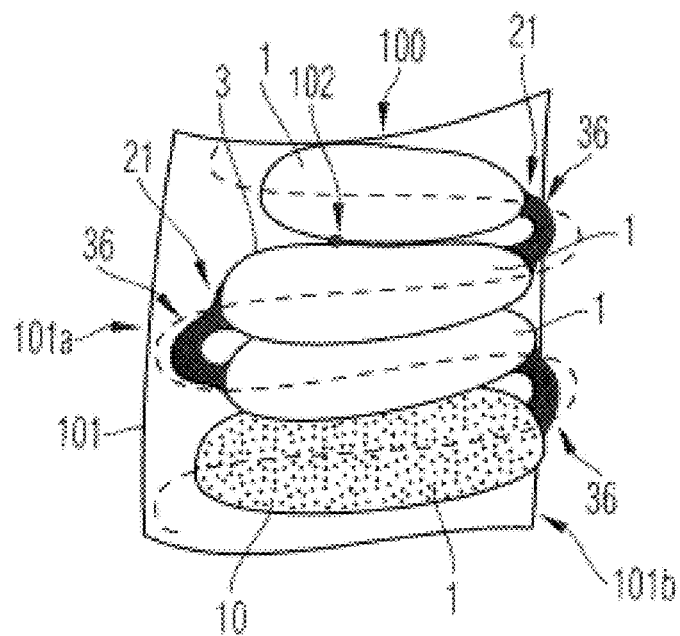
FIG. 9 schematically illustrates an arrangement comprising several units for hemostasis according to a further embodiment of the invention.
Figure 10:
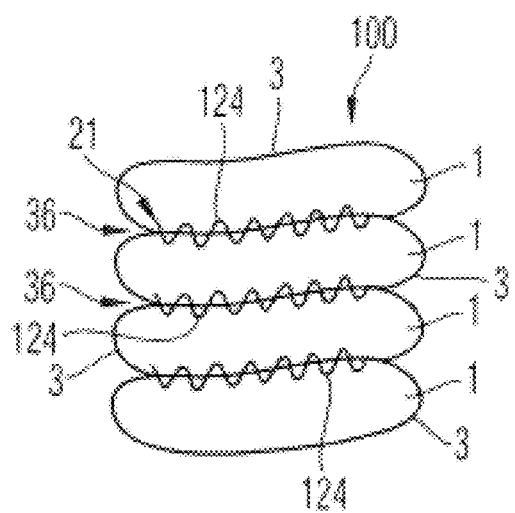
FIG. 10 schematically illustrates an arrangement comprising several units for hemostasis according to another embodiment of the invention.

The units 1 according to advantageous variants of all of the embodiments described above with reference to the FIGS. 1-8 and of the embodiments described further below with reference to FIGS. 9 and 10 are conceived to be able to remain in the body of a patient, the components of the units 1, including the envelope 3, being in these variants biodegradable. Yet, in each of the embodiments of FIGS. 1-10, by accordingly selecting the starting material 4, an envelope 3 may instead be provided which is not, or not entirely, biodegradable, and which is removed from the wound at a later time.

In the embodiments explained above with reference to the FIGS. 1-8 or explained below with reference to the FIGS. 9 and 10, instead of the mesh-type starting material 4 for forming the envelopes 3, a foil-type material 4 could be used. In this case, the hemostatic material 10 could alternatively be provided in the form of a powder, which is enclosed in the inner space 6 of the foil-type envelope.

FIGS. 9 and 10 show arrangements 100 according to still further embodiments of the invention. Each arrangement 100 in FIGS. 9 and 10 comprises several units 1 for hemostasis.

The units 1 of the arrangement 100 schematically displayed in FIG. 9 are arranged in series, are each shaped in a sausage-like manner, similar to the units 1 e.g. in FIGS. 1-3, and consecutive units 1 are connected to each other. Inner spaces of consecutive units 1 are, in the embodiment of FIG. 9 as well, separated from each other by a neck region 36. The envelope 3 of each unit 1 transitions into the neck region 36 in an area 21. The units 1 may be formed and connected to each other as described above, for example with reference to FIGS. 1-8, and may in particular be formed and connected as explained above with reference to FIGS. 1-3.

However, in the embodiment of FIG. 9, the units 1 are arranged alongside each other along their longitudinal axis, in such a manner that in combination of the units 1, the outline formed by the units 1, which are of substantially equal shape, is substantially rectangular. In FIG. 9, the outline is schematically indicated by reference numeral 101. FIG. 9 also shows that in this embodiment, the neck regions 36 are arranged in alternating manner on the left- and righthand sides 101*a* and 101*b* of the outline 101. The arrangement 100 of FIG. 9 may be obtained, for example, by arranging the chain of units 1 of FIGS. 1-3 in a sinuous manner, as schematically indicated using the dashed line in FIG. 9.

In FIG. 9, the three-dimensional units 1 therefore in combination form a larger pillow or pillow-shaped arrangement, wherein the pillow as a whole has two principal directions of extension and the thickness of the pillow substantially corresponds to the width or diameter of the units 1. Inner spaces of the units 1 form, in FIG. 9, chambers of the pillow, and in these chambers, the hemostatic material 10 is disposed, as depicted in FIG. 9 for one of the units 1 in exemplary manner. In order to retain the arrangement of units 1 as shown in FIG. 9, the units 1 may be fastened to each other e.g. in locations of additional connection 102, for example in a manner which makes it possible to separate by hand one or more of the units 1 from the pillow-shaped arrangement 100, if desired. The fastening may be accomplished, if desired, e.g. by seams, welding, clips, staples or adhesive bonding, connecting adjacent sides of adjacent units 1, in a manner similar to what has been described above with reference to FIGS. 6A-E. It is also conceivable to provide predetermined breaking points in order to make simple manual separation of one or more of the units 1 possible.

In a variant of the embodiment of FIG. 9, it is conceivable to fasten individual units 1 to each other which initially are not connected in neck regions 36, in other words, for example by arranging several elongated, e.g. sausage-shaped units 1 alongside each other so as to form the pillow-shape of FIG. 9 and fastening these units 1 then to each other so as to retain the overall shape of the arrangement 100.

As can be appreciated, units 1, which e.g. may be individual units 1 or may be connected in chain-like manner, can be arranged to form a desired overall shape or outline, e.g. the outline of a pillow, and, if desired, may be fastened to each other to retain the overall shape.

FIG. 10 shows that a pillow-shaped arrangement 100 can be formed by providing a starting material which may be hose-shaped or bag-shaped, for example, and may besides correspond to the starting material for the envelopes 3 of the units 1 as described above, and by subdividing the entire starting material into individual chambers. Each of the chambers then can form a unit 1 for hemostasis, and has an inner space (not shown in FIG. 10) in which an effective amount of hemostatic material 10 is disposed. The pillow-shaped arrangement 100 is, in FIG. 10, divided into individual chambers by relatively large seams 124, which extend along the entire width or length of the pillow, taken along the longitudinal direction of the elongate chambers. In this manner, envelopes 3 of the units 1 for hemostasis of the arrangement 100 of FIG. 10 are closed in neck regions 36 between two adjacent units 1 by the seams 124.

In FIG. 10, the inner spaces (not shown) of two adjacent units 1 are thus separated from each other by a single seam 124. Alternatively, several parallel seams can be provided in a manner similar to FIG. 6B. Furthermore, instead of seams, the other ways of closing envelopes 3 of units 1 for hemostasis in the neck regions 36, explained above with reference to FIGS. 6A, 6C, 6D, 6E may each be used in the arrangement 100 of FIG. 10. Moreover, between adjacent units 1 of the arrangement 100 of FIG. 10, a predetermined breaking point may also be provided as described above with reference to FIGS. 6A-E, 7A-C, in order to make it possible to easily detach one or more of the units 1 from the arrangement 100.

In the embodiment of FIG. 10, therefore, a larger pillow-type object is subdivided e.g. by seams 124 into a plurality of chambers, forming units 1. The arrangement and number of chambers may, however, be varied according to requirements.

Regarding the materials used to form the envelopes 3 and the starting material, and regarding the hemostatic material 10, reference is made to the explanations above, also for the embodiments of FIGS. 9-10.

While the present invention has been completely described above with reference to preferred embodiments, the invention is not limited thereto, but may be modified in many ways. The invention will be further explained by the enclosed working examples:

Examples

The following working examples provide test results achieved with hemostatic units according to the invention. The products tested comprise a modified starch granulate as a hemostatic material enclosed by a reticular polymer (PVA) having a sock-like configuration. This hemostatic unit can be combined with further units to obtain a chain as it has been described above. Between the individual hemostatic units there are predetermined breaking points so that the individual hemostatic unit can be easily removed from the chain. All components of the hemostatic unit are biodegradable and bioresorbable and may remain in the human body after application.

In use, the hemostatic unit is directly applied onto a bleeding wound or tissue. After contact with blood, the blood enters the pores of the reticular envelope material and results in swelling and gel-forming of the granulate. The granulate binds liquid components of the blood due to its hydrophilic characteristics.

At the same time, the reticular polymeric material forming the envelope dissolves in a couple of seconds thus completely releasing the granulate. At the bleeding source, solid blood components are enriched (since liquid blood components are withdrawn) thereby accelerating natural hemostasis without any chemical or pharmaceutical interaction. After successful hemostasis the wound is surrounded by a stable and firmly adhering gel layer. This layer serves as an additional barrier protecting the wound from any additional bleeding.

A hemostatic unit of the invention termed ATR 3.0 is shown in FIGS. 2 and 3.

Prototypes Used and Tested

Details on the prototypes of the unit for hemostasis used in the following tests (termed "ATR 3.0" and "ATR 4.0") can be derived from the following table 1:

TABLE 1

| | Prototypes | | | | | | |
|---|---|---|---|---|---|---|---|
| Prototype | Length [mm] | Diameter [mm] | Weight [g] | Filling rate [%] | Granulate Diameter Ø [mm] | Granulate porosity [%] | Mesh width of polymer net d90 [mm] |
| ATR_3.0 | 59 | 34 | 14.5 | ca. 90 | 2 | ca. 80 | 1.75 |
| ATR_4.0 | 97 | 21 | 10.6 | ca. 60 | 2 | ca. 80 | 1.75 |

Figure 11:
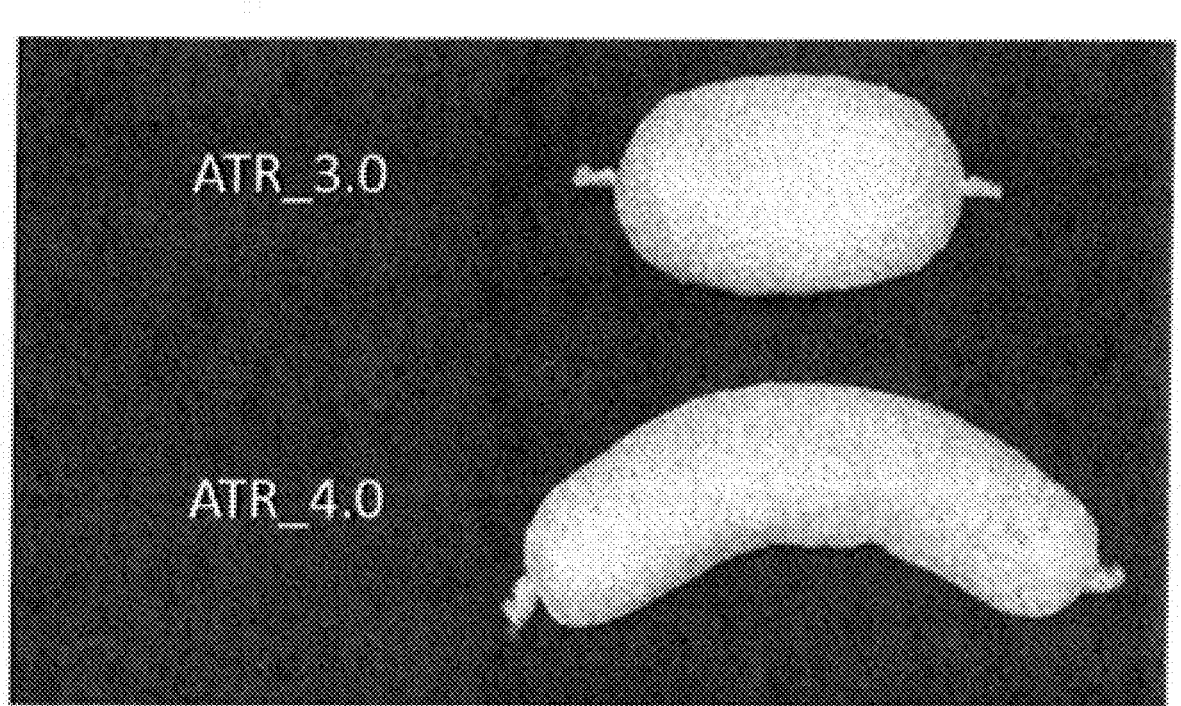
FIG. 11 A-C presents further details of a hemostatic unit of the present invention (FIG. 11 A) and its components (granulate (FIG. 11 B, left photo below) made from plant starch and the reticular envelope made from PVA (FIG. 11 C, right photo below)).
Figure 11:
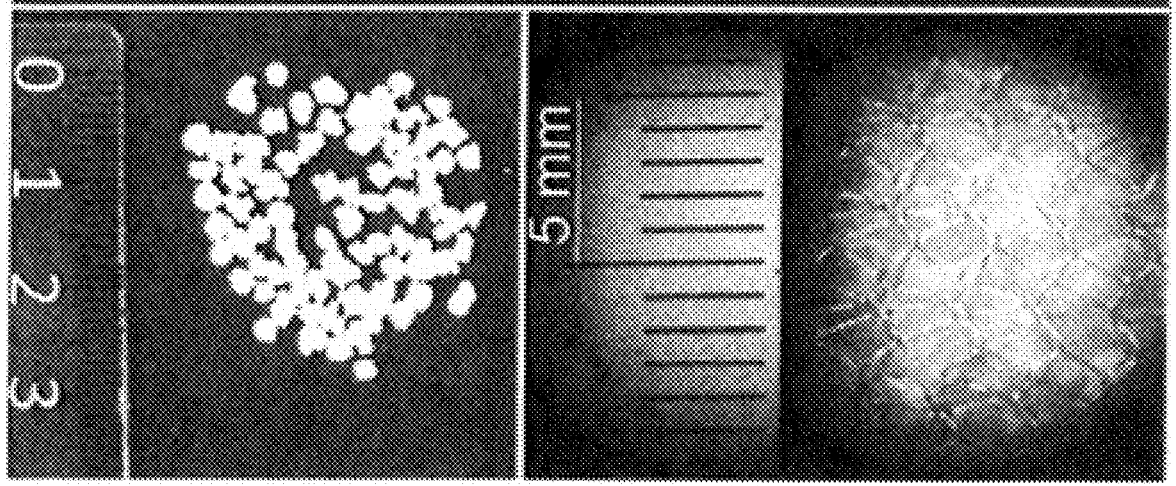

FIG. 11 presents further details of the hemostatic unit (FIG. 11 A) and its components (granulate (FIG. 11 B, left photo below) made from plant starch and the reticular envelope made from PVA (FIG. 11 C, right photo below)).

Mechanical Characteristics

In order to guarantee safe and reliable use in practice, the hemostatic unit must withstand external mechanical influences, i.e. damages of the outer envelope or of the granulate. The hemostatic unit should not allow the leakage of granulate after bending/folding of the hemostatic unit.

Figure 12:
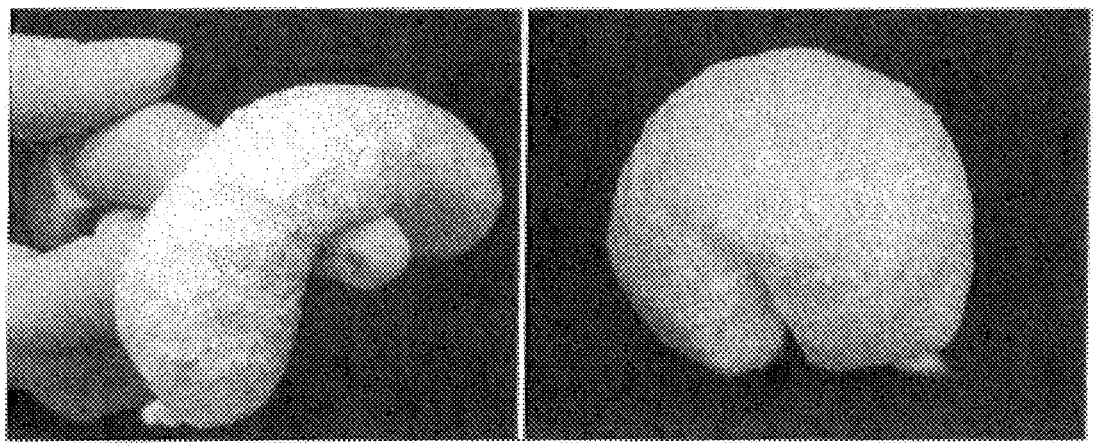
FIG. 12 A, B illustrates the flexibility of prototype ATR 4.0 comprising lower filling grade than ATR 3.0.

The prototypes have a different filling grade and thus show different characteristics. ATR 3.0 has a higher filling grade and thus has a more compact form. In contrast, ATR 4.0 is more flexible due to its lower filling grade so that even spherical geometries could be realized (see FIG. 12).

As a result, both prototypes showed a good mechanical stability. No leakage of granulate could be seen even after intensive handling of the prototypes.

Characteristics after Contact with Liquid

In the following test, the characteristics of the prototypes after contact with liquids were analyzed. The main purpose of the analysis was directed to characteristics such as soaking speed, plasticity after dissolving of the reticular envelope material and stability of the gel formed from the granulate after contact with the liquid.

The prototypes are located in a glass bowl filled with colored water (150 ml) until the dissolution of the reticular material could be seen. A subsequent modeling and reforming of the still swelling granulate mass should mimic the lining of wound surfaces and the penetration behavior of the gel into wound cavities. In particular, the strength of the gel and its adhesiveness were carefully monitored since these are essential characteristics of the hemostatic unit in terms of hemostasis. FIG. 13 shows the sequence of the test in chronological order for prototype ATR 3.0.

As can be seen, after contact with the liquid the prototype shows a rapid soaking of liquids. The reticular material is dissolved within the first fifteen seconds after contact with the liquid (FIG. 13 B) and, remarkably, the still swelling granulate could be freely reformed and modeled after dissolution of the reticular material (FIG. 13 C).

Within two minutes after contact with the liquid, a solid and consistent gel structure was formed which showed a high stability as well as a good adhesiveness after 100 seconds (see FIG. 13 F).

Furthermore, the prototype was subjected to a swelling test which showed that the overall weight of the hemostatic unit after swelling was 40 times that of the original prototype.

Swelling Behavior Depending on the Porosity and Size (Diameter) of the Granulate In order to find out more information on the granulate used as the hemostatic material, three granulates made from modified potato starch where analyzed in view of the impact of porosity and diameter of the particles on the swelling behavior.

TABLE 2

Modified potato starch granulates analyzed

| Granulate | Granulate Ø [mm] | Granulate Porosity [%] |
|---|---|---|
| GL_0.5 | 0.5 | ca. 60 |
| GB_0.5 | 0.5 | ca. 80 |
| GB_2.0 | 2.0 | ca. 80 |

For each test, the same amounts of granulate (0.5 g) were placed into a glass bowl containing colored water (20 ml) and swelling occurred for 60 s. A clear difference and a swelling behavior of the particles could be shown depending on porosity. Granulate GB 0.5 having a higher porosity of 80% was completely gelled after 60 s, whereas granulate GL 0.5 having a porosity of 60% still had a solid core of non-gelled particles after that time.

Furthermore, the size (diameter) of the granulate has an impact on the soaking speed. Although granulate GB 2.0 has the same porosity than GB 0.5, the larger particle size (diameter of 2 mm) results in a solid core of the particles as well, measured after 60 s.

SUMMARY

The prototypes analyzed showed good mechanical characteristics. They may be adapted to a specific wound geometry or strong local bleeding.

Both prototypes showed a rapid soaking of liquids.

Therefore, compared to the products already available on the market, the present hemostatic unit has the following advantages:

Compact assembly of separate hemostatic units giving the option of using one or more of those hemostatic units depending on the specific purpose
Rapid soaking speed combined with a high soaking capability
Modelling of the hemostatic unit even after swelling and gel formation in order to adapt the hemostatic unit to narrow and deep wound cavities
100% resorbable by the human body/biodegradable (no post-surgery removal of the hemostatic unit required)
The material used for hemostasis is made of pure starch
No animal based components present so that allergic reactions can be avoided

LIST OF REFERENCE NUMERALS 1 unit
2a first end (unit)
2b second end (unit)
3 envelope
4 starting material
4' remaining portion (starting material)
4a reticular-type material portion
4b foil-type material portion
6 inner space
7 interior region
10 hemostatic material
12 charge
15 starting material
21 area
22 knot
23 weld
24 seam
25 clip
26 staple
27 adhesive bonding region
36 neck region
45 breaking point
55 perforation
56 transition
57 weakened region
66 sample of starting material
78 tab
100 arrangement
101 outline
101a side (outline)
101b side (outline)
102 location of additional connection
124 seam
L length (unit)
L' length (tab)
D diameter (unit)
W width (unit)

The invention claimed is:

1. A unit for hemostasis, wherein the unit is configured to be directly applied to a bleeding wound and comprises an envelope enclosing an inner space as well as an effective amount of a hemostatic material disposed within the inner space,
wherein the unit comprises a biodegradable and/or bioresorbable, hemostatic material forming a gel after contact with aqueous liquids, where the hemostatic material is in the form of particles or granules having an average diameter of 0.5-2 mm and a porosity of 70-85%, and wherein the unit has a filling grade of 50-90 Vol %.

2. The unit according to claim 1, wherein the envelope comprises a reticular material and/or a material formed from fibers.

3. The unit according to claim 1, wherein the envelope comprises a textile or a material formed as a fleece or a wadding or a foil.

4. The unit according to claim 1, wherein the envelope is closed at both ends of the unit by a knot, a weld, a seam, a staple/or clip or adhesive bonding, and/or wherein a length of the unit is between 0.5 cm and 30 cm and/or an outer diameter or width of the unit is between 0.5 cm and 20 cm.

5. The unit according to claim 1, wherein the envelope is biodegradable entirely or in part.

6. The unit according to claim 1, which is totally bioresorbable and/or biodegradable.

7. The unit according to claim 1, wherein the hemostatic material is native or modified starch, oxidized cellulose, chitosan or a mixtures thereof.

8. The unit according to claim 1, comprising a biodegradable envelope material that is, reticular or in the form of a mesh.

9. The unit according to claim 8, where the dimensions of the unit are 10 cm×2 cm, or 6 cm×3 cm, where the unit is closed at two ends and/or wherein the hemostatic material is modified potato starch and the envelope material is a PVA mesh.

10. An arrangement of two or more units for hemostasis according to claim 1, wherein the units are coupled to each other.

11. The arrangement according to claim 10, wherein the units are arranged in series, wherein consecutive units are connected to each other.

12. The arrangement according to claim 10, wherein the envelopes of the units are formed in one piece with each other, and/or wherein the arrangement is partitioned for forming several units by a neck region or several neck regions, the inner spaces of consecutive units being separated from each other by the neck region or one of the neck regions.

13. The arrangement according to claim 10, wherein the arrangement is configured such that the units are separable from each other and/or wherein between adjacent units, a predetermined breaking point is provided.

14. A method for producing an arrangement of units for hemostasis according to claim 11,
wherein the method comprises disposing a charge of an effective amount of a hemostatic material within an interior region of a starting material, and forming neck regions on both sides of the charge so as to form an envelope enclosing the charge, wherein the hemostatic material is biodegradable and/or bioresorbable and forms a gel after contact with aqueous liquids, the hemostatic material being in the form of particles or granules having an average diameter of 0.5-2 mm and a porosity of 70-85%, and wherein the units of the arrangement produced each have a filling grade of 50-90 Vol %.

15. The unit according to claim 4,
wherein the unit is 6 cm long and/or 3 cm in diameter.

16. The unit according to claim 1,
wherein the envelope is not biodegradable.

17. The unit according to claim 1,
wherein the envelope comprises a synthetic material.

18. The unit according to claim 1,
wherein the envelope comprises a natural material.

19. The unit according to claim 1,
wherein the envelope comprises a combination of at least one synthetic material and at least one natural material.

20. The unit according to claim 1,
wherein the envelope comprises a synthetic polymeric material or a natural polymeric material or a combination of at least one synthetic polymeric material and at least one natural polymeric material.

21. The arrangement according to claim 12,
wherein the envelopes of the units are formed in one piece with each other from a hose-shaped starting material.

22. The arrangement according to claim 10,
wherein between adjacent units, a predetermined breaking point is provided, which is formed by a perforation, or by a transition, within the material of the envelope, from a reticular material or a material made from fibers to a foil material, or by a weakened region of textile in the area of the predetermined breaking point.

23. The arrangement according to claim 11,
wherein the units are arranged in the form of a chain.

* * * * *